United States Patent
Cannara et al.

(10) Patent No.: US 10,126,255 B2
(45) Date of Patent: Nov. 13, 2018

(54) HIGH EFFICIENCY PHOTON DETECTION

(71) Applicant: Elwha LLC, Bellevue, WA (US)

(72) Inventors: Rachel Cannara, Kirkland, WA (US); Fred Sharifi, Kirkland, WA (US); Alex Smolyanitsky, Boulder, CO (US)

(73) Assignee: Elwha LLC, Bellevue, WA (US)

( * ) Notice: Subject to any disclaimer, the term of this patent is extended or adjusted under 35 U.S.C. 154(b) by 44 days.

(21) Appl. No.: 15/379,006

(22) Filed: Dec. 14, 2016

(65) Prior Publication Data

US 2017/0205361 A1 Jul. 20, 2017

Related U.S. Application Data

(60) Provisional application No. 62/267,677, filed on Dec. 15, 2015.

(51) Int. Cl.

| | |
|---|---|
| *H01L 27/146* | (2006.01) |
| *G01N 23/20066* | (2018.01) |
| *G01N 23/046* | (2018.01) |
| *A61B 6/03* | (2006.01) |
| *G01V 5/00* | (2006.01) |

(52) U.S. Cl.
CPC ..... *G01N 23/20066* (2013.01); *G01N 23/046* (2013.01); *A61B 6/032* (2013.01); *G01N 2223/063* (2013.01); *G01N 2223/501* (2013.01); *G01V 5/005* (2013.01)

(58) Field of Classification Search
CPC .................................................. G01T 1/2928
See application file for complete search history.

(56) References Cited

U.S. PATENT DOCUMENTS

| | | | | |
|---|---|---|---|---|
| 2009/0032717 A1* | 2/2009 | Aykac | ........... | G01T 1/2018 250/367 |
| 2011/0122998 A1* | 5/2011 | Proksa | ........... | G01T 1/2928 378/154 |

FOREIGN PATENT DOCUMENTS

| | | | | | |
|---|---|---|---|---|---|
| GB | | 1471032 A | * | 4/1977 | ............ G01J 5/34 |
| WO | WO | 2008059425 A2 | * | 5/2008 | ........... G01T 1/2928 |

OTHER PUBLICATIONS

M J Yaffe and J A Rowlands, Imaging Research Program, Sunnybrook Health Science Centre, The University of Toronto, Phys. Med. Biol. 42 (1997)1-39. Printed in the UK, n final form Aug. 16, 1996, 30 pages.

A.A. de Carvalho, A.L. Brassalotti, M.H. de Paula and A.J. Alter, Use of lithium niobate detector for measuring X-ray intensity in mammographic range, Electronics Letters Sep. 2, 2004, vol. 40, No. 18, 2 pages.

(Continued)

*Primary Examiner* — Kiho Kim

(74) *Attorney, Agent, or Firm* — Polsinelli LLP; Kory D. Christensen

(57) ABSTRACT

A detection pixel includes a material that is chosen so that its (averaged) atomic number density leads to the Compton process being the dominant scattering mechanism in response to incident photons, leading to production of Compton electrons with sufficient number and kinetic energy to produce an electric or magnetic response in the material. The incident photon and Compton electrons each have a characteristic travel distance in the material, and the detection pixel has at least one dimension that is selected according to a range defined by these characteristic travel distances. The detection pixels may be arranged in an array for imaging.

42 Claims, 8 Drawing Sheets

(56) References Cited

OTHER PUBLICATIONS

D.B. Li, D.R. Strachan, J.H. Ferris and D.A. Bonnell, Polarization reorientation in ferroelectric lead zirconate titanate thin films with electrons beams, J. Mater. Res., vol. 21, No. 4, April, pp. 935-940.
W. Lee et al., Letters, Individually addressable epitaxial ferroelectric nanocapacitor arrays with near Tb inch-2 density, Published online: Jun. 15, 2008; doi: 10.1038/nnano/2008.161, nature nanotechnology, vol. 3, Jul. 2008, 6 pages.

* cited by examiner

HIGH EFFICIENCY PHOTON DETECTION

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

This application claims priority under 35 U.S.C. § 119(e) to Provisional Patent App. No. 62/267,677, filed on Dec. 15, 2015, titled "High Efficiency Photon Detection," which application is hereby incorporated by reference in its entirety.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In one embodiment, an apparatus comprises: a detection pixel including a first material that is responsive to incident photons to produce Compton electrons and an electric or magnetic response in the first material, wherein the incident photons and the Compton electrons each have a characteristic travel distance in the first material; and wherein the detection pixel has at least one dimension that is selected according to at least one of the characteristic travel distance of the incident photons and the characteristic travel distance of the Compton electrons.

In another embodiment, a system comprises an array of detection pixels, each detection pixel in the array of detection pixels including a first material that is responsive to incident photons to produce Compton electrons and an electric or magnetic response in the first material, wherein the incident photons and the Compton electrons each have a characteristic travel distance in the first material; and wherein each detection pixel in the array of detection pixels has at least one dimension that is selected according to at least one of the characteristic travel distance of the incident photons and the characteristic travel distance of the Compton electrons.

In another embodiment, an x-ray imaging system comprises: a source of x-rays; an array of detection pixels, each detection pixel in the array of detection pixels including a first material that is responsive to the x-rays to produce Compton electrons; and detection circuitry operably connected to the array of detection pixels and configured to measure a change in the first material produced by the Compton electrons.

In another embodiment, a method corresponding to a detection pixel including a first material having an electric or magnetic response to electromagnetic energy comprises: receiving information corresponding to a resonance of a detection circuit that includes the detection pixel, wherein the resonance is characterized by a resonant frequency and a linewidth; and determining a change in the resonant frequency of the detection circuit to determine the presence of electromagnetic energy in the detection pixel.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
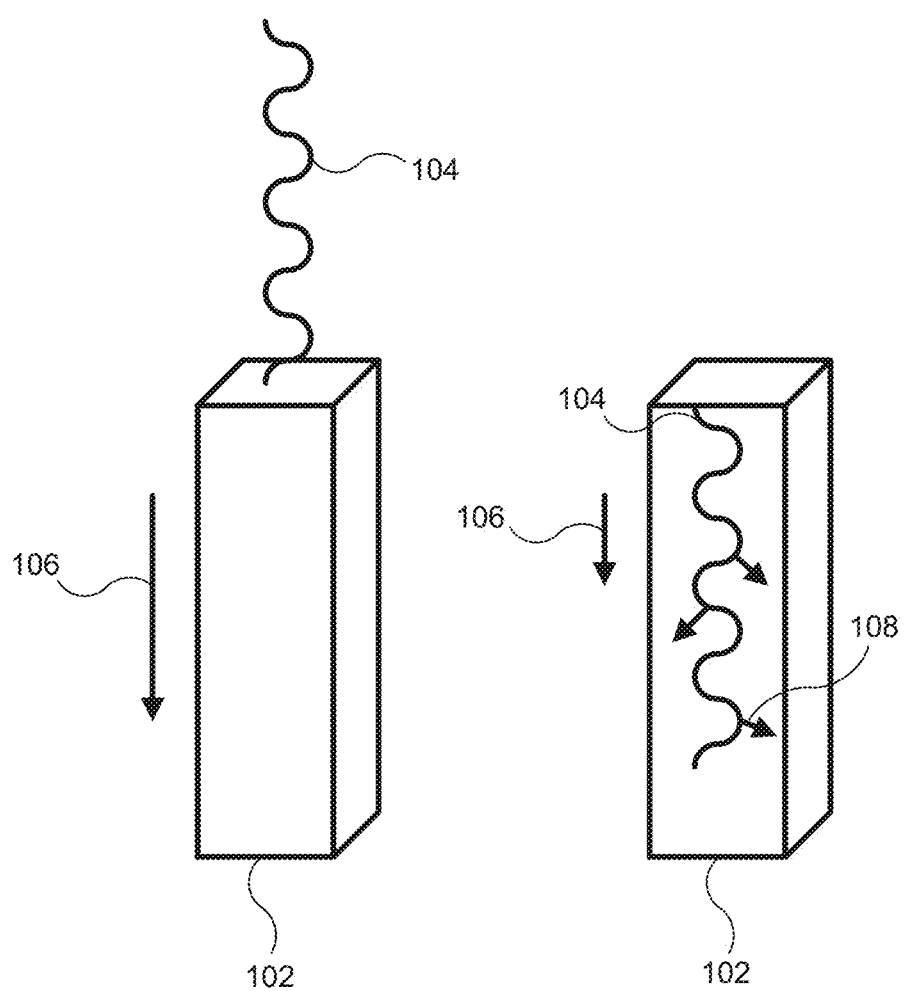
FIG. 1 is a schematic of a detection pixel.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 shows an embodiment of an apparatus configured to detect high energy electromagnetic radiation, where photons 104 are incident on a pixel 102 that includes a material that is responsive to incident photons in an energy range characteristic of, for example, x-rays and gamma rays (including, but not limited to, energies in the range of 20 kilo-electron-volts (KeV) to 5 mega-electron-volts (MeV)) to produce a change in dielectric constant or magnetic permeability. This change in the dielectric constant or magnetic permeability arises from production of Compton electrons by collision with the incident photons, which travel through the material to produce a measurable change in the dielectric and/or diamagnetic properties of the material. The material composition of the pixel 102 is chosen to have the appropriate averaged atomic density so that the Compton process dominates for the photon energy of interest; this choice may be dependent on the specific application. This mode of scattering results in energy transfer to an ejected outer-shell electron, and produces a volume of interaction as the electron travels through the lattice, which will be described in greater detail herein. The interaction creates a transient distortion of the lattice, which manifests itself through a change in the dielectric constant and/or magnetic permeability of the detector material. These changes in the dielectric constant and/or magnetic permeability can be measured electronically and/or optically to allow detection of an incident photon in the energy range described above. This measurement is achieved through the appropriate electronic and/or optical connection of the detector element to the appropriate circuitry, and detection methods will be described further herein.

In some embodiments the material of the pixel 102 includes a ferroelectric material, a piezoelectric material, or a multiferroic material. These materials may have values of electronic and magnetic permeability that change when exposed to incident photons in the energy range of interest. Examples of ferroelectric materials include, but are not limited to, titanates of lead, bismuth, barium, zirconium, and their alloys (a prototype being lead-zirconate-titanate, i.e., PZT) which would be appropriate for the higher energy range of photons. An example of a material that exhibits both ferroelectricity and piezoelectricity is a non-linear optical material such as lithium niobate, which would be appropriate for the lower energy range of the photons, and where the detection may be through optical methods. Examples of multiferroic materials include perovskites such as bismuth manganite, bismuth ferrite, and the related family of transition metal and rare earth manganites and ferrites. Other multiferroic materials include the non-perovskite and non-oxide compounds such as spinel compounds.

In one exemplary embodiment, the pixel 102 includes a ferroelectric material, and the dimensions and material of the pixel 102 are selected according to the following considerations. The detector can be configured such that the volume of interaction is comparable to the volume of an individual pixel, to yield a measurable response. The material is chosen so that the Compton scattering process dominates over the photoelectric scattering process for the incident high energy photons used in the specific application. The incident photons and the Compton electrons each have a characteristic travel distance in the material, which is dependent on the energy of the incident photons and the average atomic density of the detector material. In the scattering process, the incident photon travels a distance $L_1$ before a scattering event, leading to a Compton electron. As the fraction of energy that is transferred to the Compton electron is large, the Compton electrons 108 will then have a high kinetic energy and a travel length $L_2$ that is significant. As these electrons 108 travel through the material, they disturb the lattice structure sufficiently to reduce the intrinsic dielectric (and/or magnetic permeability) constant and yield an effective volume of interaction. Detailed calculations demonstrating these concepts are included in Appendix A, which is attached hereto. Calculations show that optimal pixel size in the range of $L_1$ to $L_2$, however actual selection of pixel size will depend on considerations specific to an application and may vary from this optimal pixel size.

In some embodiments, such as applications involving higher energy photons, the pixel 102 includes a material with relatively large atomic numbers to provide relatively higher stopping power. The higher atomic density results in relatively shorter lengths $L_1$ and $L_2$. In the calculations, for a typical material such as PZT, $L_1$ is approximately 10 micrometers and $L_2$ is approximately 2 micrometers, defining the range of dimensions for the pixel. In another example such as lithium niobate, the lower atomic number would make the material appropriate for lower energy photons, and yield larger travel lengths $L_1$ and $L_2$ while maintain a sufficient ratio. For each case, the detector pixel dimensions would be chosen accordingly.

Although the pixel 102 shown in FIG. 1 has a substantially rectilinear geometry, in other embodiments the pixel has a different shape. For example, in some embodiments the pixel may be substantially cylindrical. Further, FIG. 1 shows the pixel having a length that is greater than the cross-sectional dimension. In other embodiments, the length is less than the cross-sectional dimension. There are many different shapes that the pixel may have, and the pixel shape may be selected according to different factors such as the geometry of a system in which it is incorporated, ease of fabrication, or other considerations.

Figure 2:
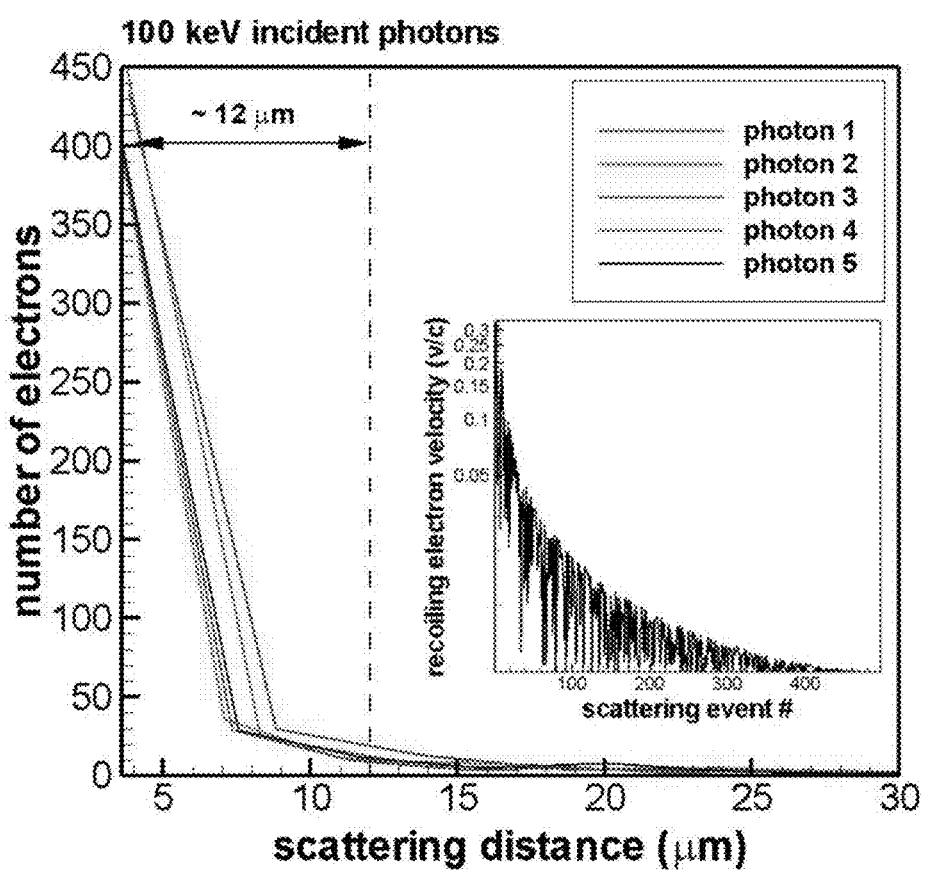
FIG. 2 is a schematic of a Monte Carlo simulation of Compton electron travel distance in PZT.

FIG. 2 shows a Monte Carlo simulation for the characteristic travel distance of the incident photon and the number and energy of Compton electrons produced by the scattering process. For this simulation, the photon energy is 100 keV and the pixel material is $PbTi_xZr_{1-x}O_3$ (PZT). This simulation shows that the characteristic travel distance of the photons is about 12 micrometers. The resulting Compton electrons have an energy of approximately 20 KeV. At this energy, the electrons will have a travel length of approximately 2 micrometers. Thus, for a pixel of this material configured to receive 100 keV photons, the cross sectional dimension of the pixel 102 may be on an order ranging from 2 to 12 micrometers. The actual cross sectional dimension may be further refined according to fabrication considerations, experimental results, or other considerations. Similar simulations may be done for other photon energies and/or other materials to determine optimal cross-sectional dimensions of the pixel.

Figure 3:
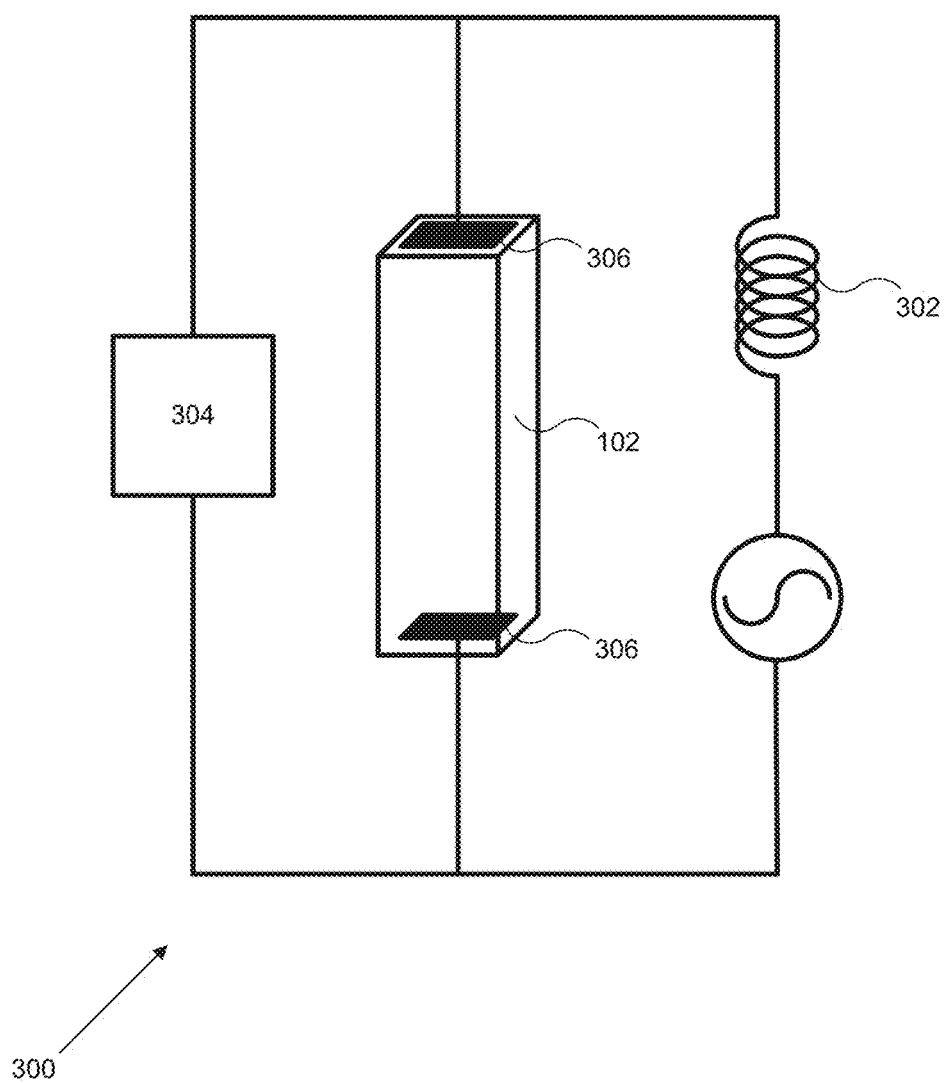
FIG. 3 is a schematic of a detection pixel with measurement circuitry.

FIG. 3 shows the pixel 102 configured in detection circuitry 300. In this embodiment the detection circuitry 300 includes the pixel 102 (configured as a capacitor), and an inductor 302, wherein the inductor and the capacitor formed by the pixel 102 form a resonant circuit. The detector may operate in either a poled (applied dc voltage bias) or non-poled configuration. The detection circuitry further includes circuitry 304 configured to determine at least one property of the resonant circuit, such as a resonant frequency. In this embodiment, electromagnetic energy incident on the pixel 102 causes a change in dielectric constant of the pixel, thereby changing its capacitance, and thereby changing the resonant frequency of the resonant circuit, which is detected by the element 304. The resonant frequency of the circuit changes according to the change in capacitance of the pixel, and thus the deviation from resonance would be a measure of the reduction in the dielectric constant, and be proportional to the intensity of the incident photons.

FIG. 3 shows the pixel 102 configured as a capacitor, where parallel conductive plates 306 are placed at opposite ends of the pixel to form a capacitor. The placement and size of these conductive plates 306 are exemplary embodiments and may vary according to a particular embodiment. For example, FIG. 3 shows the parallel conductive plates 306 being positioned on the short sides of the pixel, however in some embodiments the conductive plates 306 may be positioned along the longer sides of the pixel.

In other detection configurations, such as embodiments in which the pixel material is a multiferroic, the pixel may be configured as an inductor in a resonance circuit, operating on the same principals as a ferroelectric capacitor in a resonance circuit.

Figure 4:
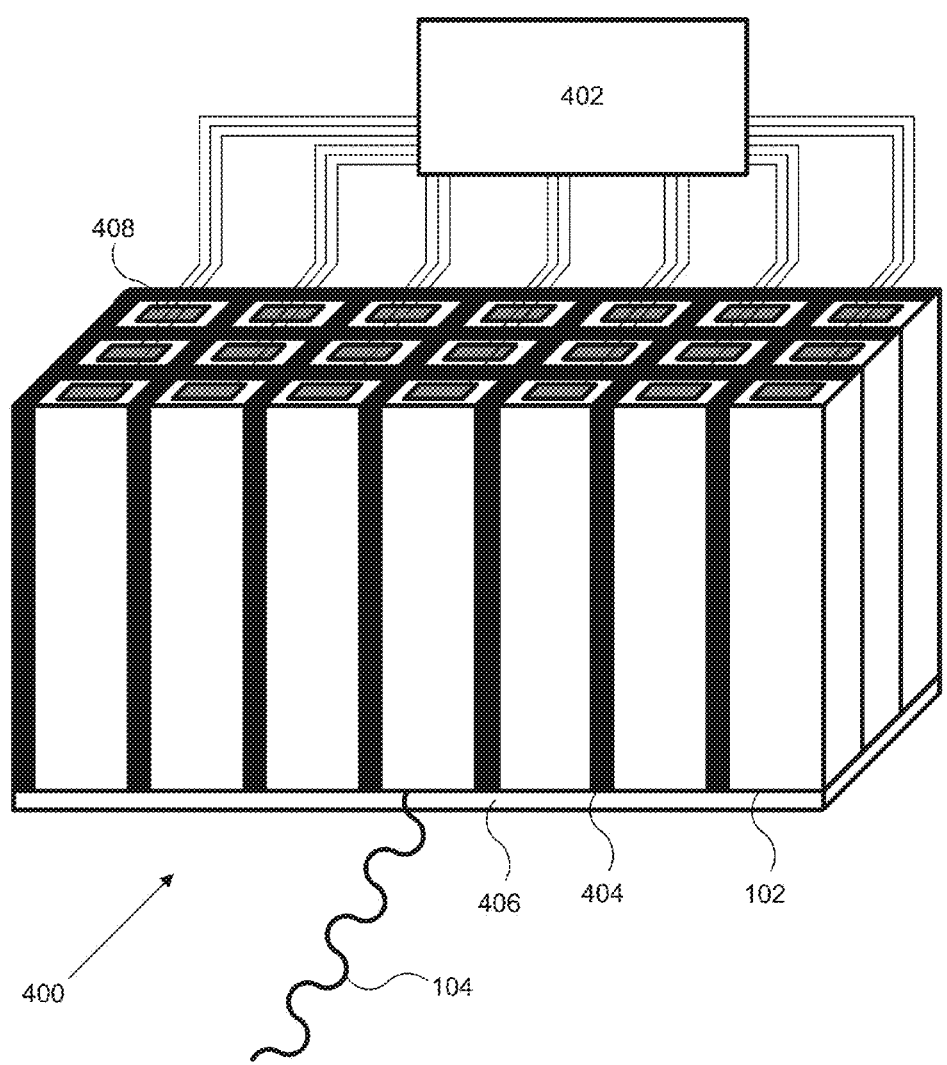
FIG. 4 is a schematic of detection pixels in a two dimensional array.

FIG. 4 shows an array 400 of the pixels 102 of FIG. 1 together with detection circuitry 402, where the detection circuitry may be configured as described with respect to FIG. 3. The array of pixels is configured on a conductive ground plate 406, and each pixel is configured with an individual conductive plate 408 such that the array of pixels forms an array of capacitors, where each of the capacitors is electrically connected to the detection circuitry. Here the pixels in the array are separated by a gap 404, where the gap may be air or another insulator with dielectric or diamagnetic properties that do not change significantly compared to the detector material. The array of FIG. 4 is two dimensional, that is, the pixels are patterned along two dimensions, however this is just one exemplary embodiment, and in other embodiments, the array is one dimensional or three dimensional.

In some embodiments the array 400 of pixels 102 forms an imaging system. The dimensions of the pixels 102 may be selected according to the considerations as previously described herein. The pixels are each operably connected to the detection circuitry 402, and the detection circuitry may include a multichannel analyzer configured to identify which pixels have received photons.

In some embodiments the pixel materials in the array are not all the same. For example, pixels having different materials may be incorporated in an array where the materials have different ranges of electromagnetic energy they are capable of detecting, thus providing for a detector with a broader range of detection capability than a detector whose pixels are all the same.

Figure 5:
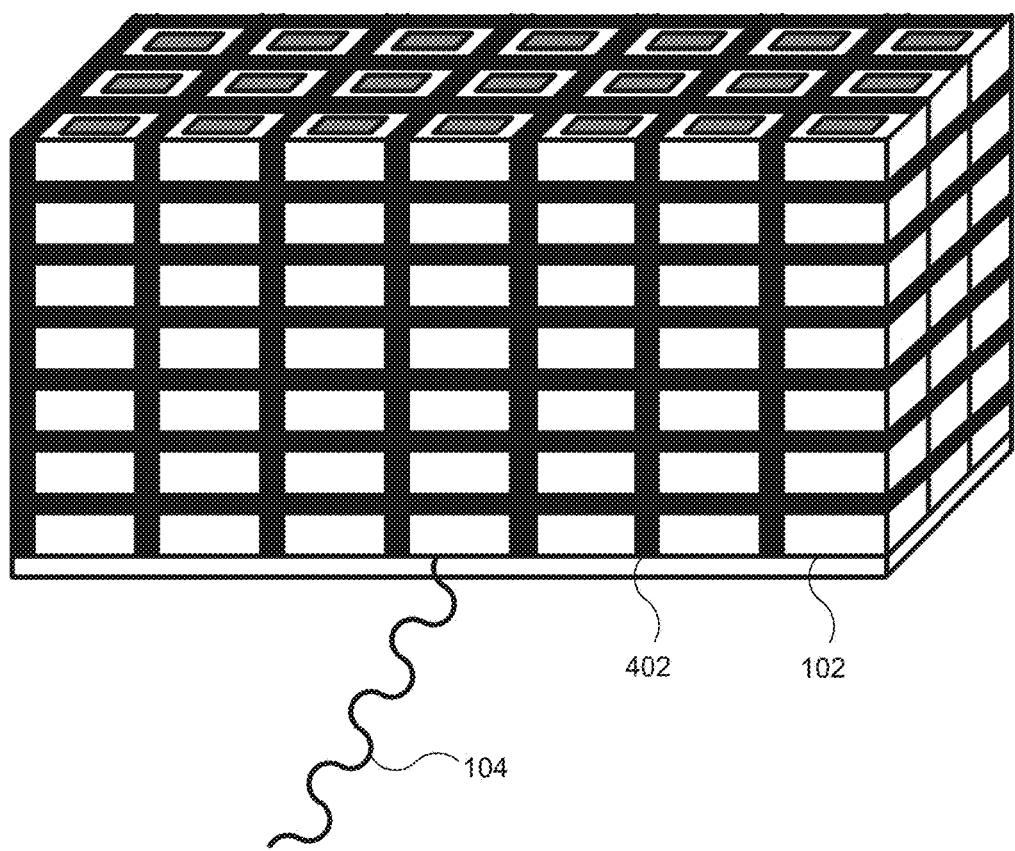
FIG. 5 is a schematic of detection pixels in a three dimensional array.

FIG. 5 shows another embodiment of an array 500 of pixels, where the array 500 shown in FIG. 5 is three dimensional. For clarity the detection circuitry is not shown in FIG. 5, however in this embodiment each pixel 102 would be configured as a capacitor and would be operably connected to detection circuitry such that the presence of electromagnetic energy in each of the pixels could be detected. Such a three dimensional arrangement would allow the system to determine spatial information and information related to the energy of the incoming photons. For example, the energy of an incoming photon could determine how far the photon would travel in the detector, which could be determined according to which detectors receive electromagnetic energy.

Figure 6:
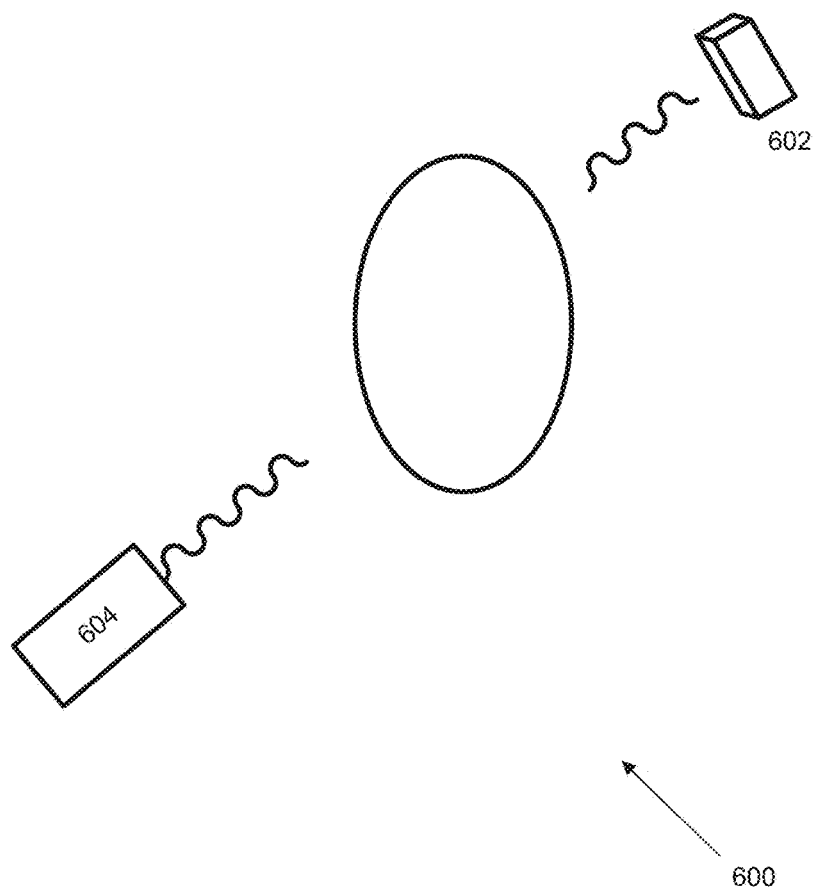
FIG. 6 is a schematic of a medical imager including one or more arrays of detection pixels.

FIG. 6 shows an array of pixels 602 arranged in an imaging system, where in some embodiments such an imaging system is an x-ray imager. The system further comprises a source of x-rays 604 that is arranged to produce photons that can pass through a subject and be received by the array of pixels 602. In some embodiments the system is a medical imaging system such as a pediatric imaging system, an emergency medical imaging system, or other type of medical imaging system. In other embodiments the system is a security system such as a system configured for airport security, for passengers or for objects. In other embodiments, the system is a security system used for detection of gamma rays with energy in the range of MeV, sourced from special nuclear materials. In other embodiments, the system is a medical system used to track the location of radioactive tags used in diagnostic medical imaging. There are many ways of configuring the imaging system and the system may be applied to a wide range of different subjects.

The system includes detection circuitry (not shown) as previously described herein, where the detection circuitry is operably connected to the array of detection pixels and configured to measure a change in the first material produced by the Compton electrons, again as previously described herein. In some embodiments the detection circuitry is configured to compute a tomographic image of a subject, i.e., a CT scan. The source of x-rays and the array of detection pixels may be configured on a stage or other type of mount that is movable relative to a subject in order to scan the subject. The system may in some embodiments be configured to determine one or more properties corresponding to the incoming photons, such as an energy and/or an energy range, and/or an intensity.

Disclosed below are calculations corresponding to the high efficiency photon detection approach described herein. It is comprised of four sections describing: 1) dominance of the Compton process in comparison to the photoelectric process for the appropriate choice of material and x-ray energies, 2) demonstration of significant distortion of a prototype lattice in the presence of Compton electrons, 3) calculation of the number and travel length of the electrons for a specified x-ray energy to determine the volume of interaction and thus the size of the detector pixel, and 4) determination of single-photon sensitivity of the detector pixel.

1. Calculation of the Compton Cross-Section

Figure 7:
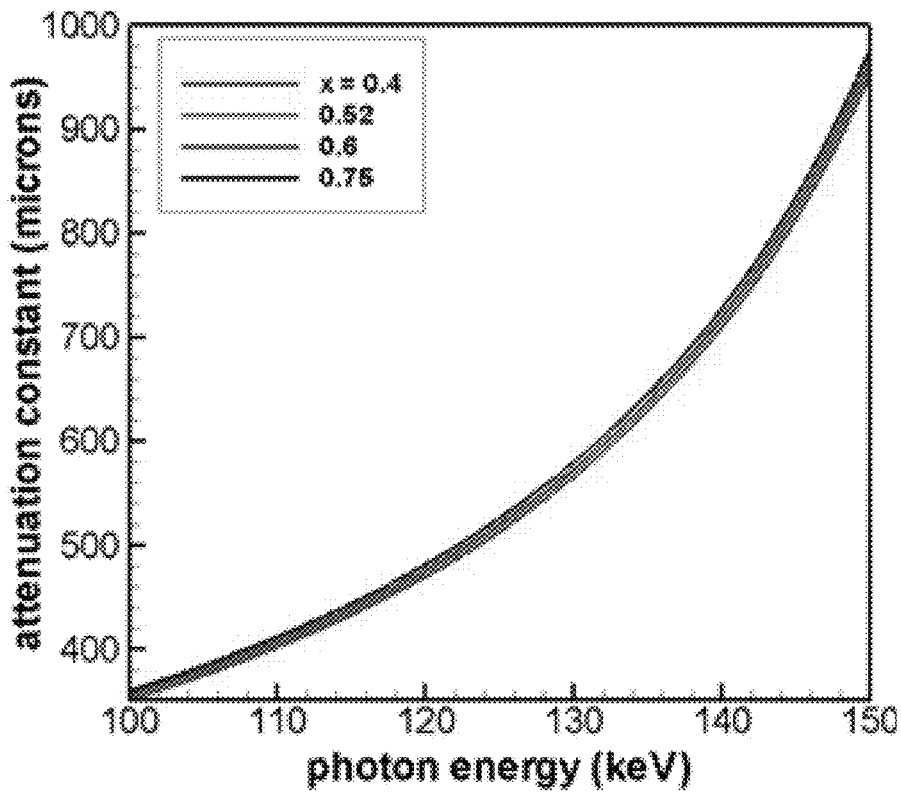
FIG. 7 is a graph of attenuation distance for $PbTi_xZr_{1-x}O_3$ as a function of incident x-ray photon energy for various compositions.

High energy photons interact with matter through several possible paths, determined by the energy of the photons and the atomic number of the constituent materials in which they travel. Classically, the sum of all these paths results in an overall intensity that drops exponentially with travel length as the x-rays are transformed into other forms of energy. The length scale over which the intensity decreases is classically characterized by a mass attenuation parameter. The $PbTi_xZr_{1-x}O_3$ (PZT) compound mass attenuation is calculated according to $$\left(\frac{\mu}{\rho}\right) = \sum w_i \left(\frac{\mu}{\rho}\right)_i, \quad (1)$$

where $$\left(\frac{\mu}{\rho}\right)_i$$

and $w_i$ are the mass attenuation constants of the constituent atoms and the corresponding atomic weight fractions, respectively. The resulting effective attenuation length calculated from the tabulated data is shown in FIG. 7.

X-ray imaging for security and medicine have energies ranging from tens to hundreds of keV. In this energy range, there are two possible interaction mechanisms: Compton and photoelectric scattering. Compton scattering results in an ejected outer shell electron and a significant portion of the x-ray energy is transferred into the kinetic energy of the scattered electron. In contrast, the photoelectric process involves scattering of inner-shell electrons, inducing an inner shell electronic transition where part of the energy is transferred to secondary x-ray photons. As the travel length of electrons is significantly shorter than photons in matter, the Compton process results in a larger quantity of energy being dissipated in a smaller volume. This causes sufficient perturbation of the lattice structure to alter its intrinsic dielectric value for a piezoelectric or ferroelectric material (and permeability in the case of a multiferroic). The result is a dramatic reduction in the large dielectric constant (permeability), yielding a measurable electronic response due to a change in the electronic impedance of the detector circuit.

The detector material should be of the appropriate atomic density so that the Compton process dominates the scattering at the operating energy of the x-ray source. The Compton process dominates at higher x-ray energies and lower (Z) detector density. Higher energy applications, such as computed tomography and security screening, would use higher (averaged) atomic number detector materials such as PZT, whereas lower energy applications would use less dense materials such as $LiNbO_3$. Calculation of the Compton cross-section also yields the average number of Compton electrons produced in the detector by a single photon, and thus the magnitude of the response (change in capacitance or inductance).

The relative probabilities of Compton scattering and the photoelectric effect can be directly assessed from the ratio between the corresponding scattering cross-sections as functions of the incident photon energy and the detector (Z) density. For Compton scattering, the well-established Klein-Nishina formalism is used:

$$\sigma_{Compton} = Z \times 2\pi r_0^2 \left\{ \frac{1+k}{k^2} \left[ \frac{2(1+k)}{1+2k} - \frac{\ln(1+2k)}{k} \right] + \frac{\ln(1+2k)}{2k} - \frac{1+3k}{(1+2k)^2} \right\}, \quad (2)$$

where $r_0 = 2.817 \times 10^{-15}$ m is the classical electron radius and $$k = \frac{h\nu}{m_e c^2}.$$

Figure 8:
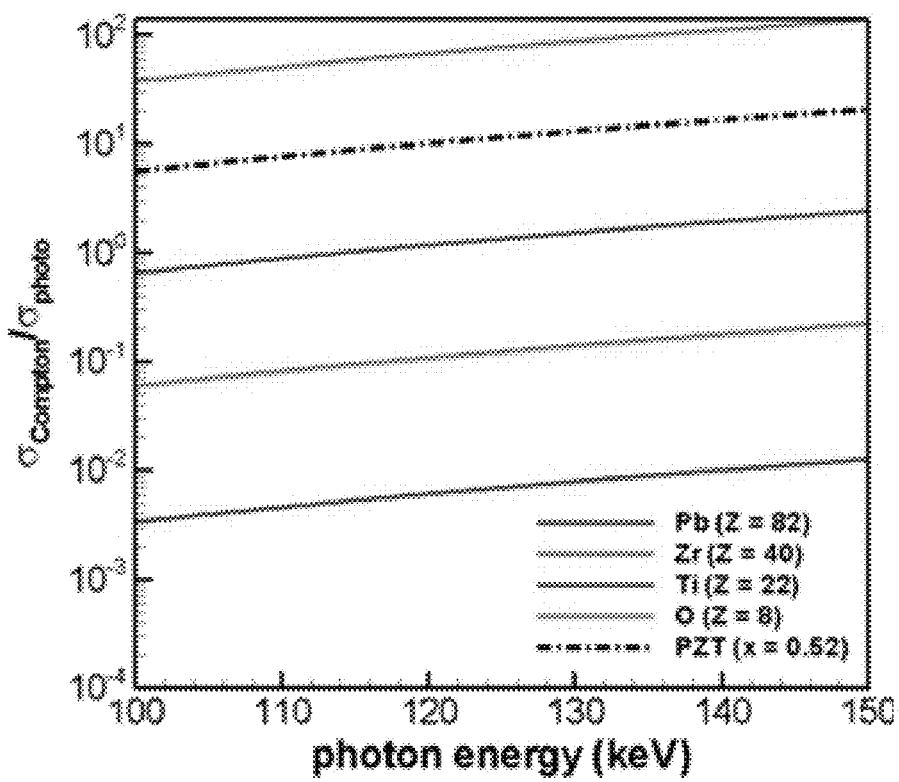
FIG. 8. is a graph of ratio of Compton and photoelectric effect cross-sections vs. photon energy for PZT.

The value of k determines whether scattering occurs within the classical or the relativistic frame of reference associated with the moving electron. For the highest incoming photon energies considered below (150 keV), k=0.29, and thus relativistic effects do not play a significant role in these considerations. The effective scattering cross-section of the photoelectric effect in the non-relativistic treatment is:

$$\sigma_{photo} = \frac{32\sqrt{2} \pi r_0^2 \alpha^4}{3} Z^5 k^{-7/2}, \quad (3)$$

where $\alpha=1/137$ is the fine structure constant. In FIG. 8, the ratio of $$\frac{\sigma_{Compton}}{\sigma_{photo}}$$

is plotted for the constituent atoms, as well as for PZT as a whole, as a function of incident photon energy.

The data in FIG. 8 indicate that the relative contribution of Compton scattering in PZT is 5.6 at 100 keV, and 20.5 at 150 keV, yielding a Compton scattering probability of 84% and 95% respectively.

Figure 9:
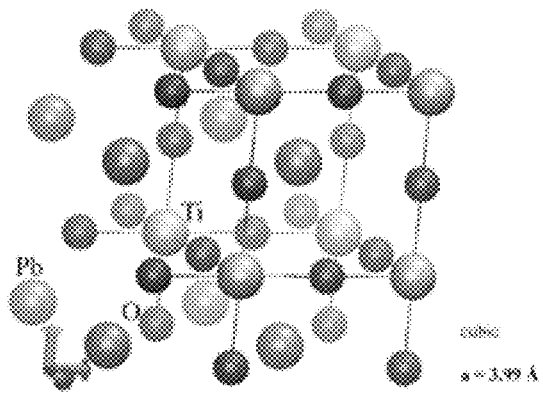
FIG. 9 illustrates an optimized electrically neutral $PbTiO_3$ structure.

2. Demonstration of Large Lattice Distortion in the Presence of Compton Electrons The dielectric constant modification by local charging, as well as by the lattice distortions caused by electric charging may be obtained by quasi ab initio density functional theory (DFT) calculations. The numerical calculation presented here is a concurrent cell and structure optimization performed at an externally applied isotropic pressure of 1.0 atm. The simulated system corresponds to x=1 ($PbTiO_3$). The simulation is implemented with use of the Perdew-Burke-Ernzerhof (PBE) exchange correlation function with the appropriately selected basis functions. The simulation utilizes the Gaussian plane wave (GPW) approach to representing the electron wave-functions within the CP2K simulator. The basic structure of the calculation is the energy-optimized electrically neutral structure shown in FIG. 9.

Positive charge: The electrically charged system (total charge +1e, or +e/8 per unit cell due to a leaving Compton electron, corresponding to the inner cone in FIG. 2), undergoes considerable local anisotropic strain, resulting in the following lattice periodicity values: X: 3.968 Å (0.55% compression), Y: 3.932 Å (1.45% compression), Z: 3.968 Å (0.55% compression).

Negative charge: Extreme anisotropic strain is observed along the X-axis. The resulting lattice periodicity is: X: 5.06 Å (27% stretching), Y: 3.86 Å (3.26% compression), Z: 3.86 Å (3.26% compression).

The anisotropy of strain indicates a significant modification of the dielectric constant from direct theoretical calculations at high charge densities. The strain values can be used for an empirically based quantitative estimation of the dielectric constant modification. Existing experimental data or the measured PZT voltage/field-to-strain constants can be used for estimation.

3. Calculation of Travel Length and Volume of Interaction

As the x-ray fluence within the material decreases exponentially with the penetration distance, the probability of Compton scattering quickly decreases with decreasing incident photon energy as the single photon continues to propagate within the detector. Thus Compton scattering only dominates the earlier stages of scattering for the selected material leading eventually to a photoelectric absorption resulting in complete absorption of the photon. To quantitatively illustrate the discussion above, a Monte-Carlo simulation of the scattering process is implemented. The Klein-Nishina description of each scattering event is used:

$$\lambda_f = \frac{1}{\left(1 - \frac{E_b \lambda_i}{hc}\right)} \left( \lambda_i + \frac{h}{mc}(1 - \cos\theta) \right), \quad (4)$$

where $\lambda_i$ and $\lambda_f$ are the photon wavelengths before and after a given scattering event, respectively; m, $E_b$, and θ are the electron's rest mass, the atomic binding energy, and the photon's scattering angle relative to its initial direction, respectively. The prefactor term does not play a significant role during the relatively early stages of the scattering process ($E_b \ll hc/\lambda_i$), which is where Compton scattering dominates, as discussed above.

The stochastic portion of the Monte Carlo simulation is set by the random scattering angle φ of the recoiling Compton electron (relative to the photon's direction prior to each scattering event). The probability distribution between φ=0 and φ=2π can be assumed to be uniform. From conservation of momentum, at every scattering event $$\cos\theta = \frac{1-\beta^2}{1+\beta^2}, \text{ where } \beta = \frac{\cot\varphi}{1+(h/mc\lambda_i)}. \quad (5)$$

The results are shown in FIG. 2. The simulations predict each single photon will yield four to ten Compton electrons with energies ranging from 10 to 25 keV. The travel length of the electrons is approximately 10 μm, establishing a typical size for a pixel element.

4. Calculation of Response to a Single X-Ray Photon

The kinetic energy of the high-energy electrons is eventually converted to lattice vibrations. The highly transient effect of the initial lattice shockwaves generated by the electrons is of interest, as it contributes to disrupting the local polarizability of the material.

The electrons undergoing collisional scattering in the crystal will produce spherical lattice shockwaves, effectively forming a conical wave-front along their paths within the detector material. Because the electrons' velocities (and energies) decrease exponentially in time, the "final" travel distance of the electron is asymptotic. The time it takes the electron to reach the asymptote is calculated to be 10 ps, which is the effective onset time for disruption. The speed of sound in PZT is $v_s$=5000 m/s, and yields a radius of the wave-front cone of 50 nm. With a travel length of a few micrometers, the effective total volume of the resulting highly perturbed lattice can be calculated.

Figure 10:
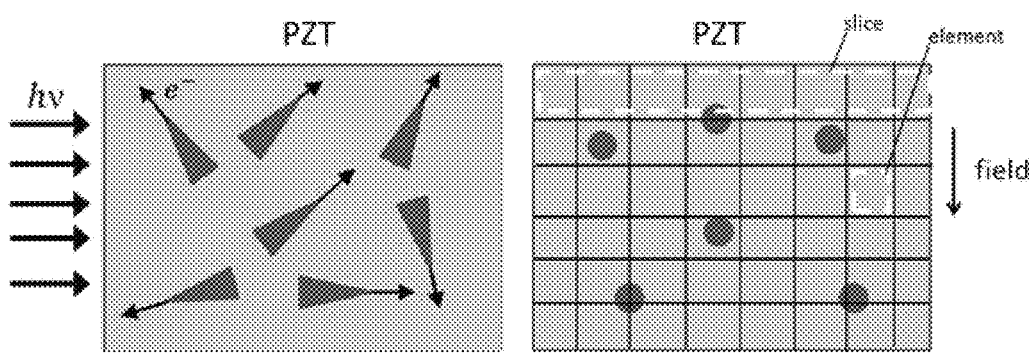
FIG. 10 is a schematic representation of the conical lattice shockwaves produced by Compton electrons and a spherical "hot-spot" approximation with mesh.

Because the orientation of the wave-fronts is spherically symmetric, a further simplification is possible as long as the effective total volume of the perturbed region is preserved (right pane of FIG. 10). With a probe field as shown in the right pane of FIG. 10, a direct estimate of the effect on the overall effective device capacitance (and dielectric constant) is possible.

Assuming the geometry and the rectangular mesh as shown in the right pane of FIG. 10, the effective volumetric "hot spot" density is $$\rho = \frac{N}{Ad}, \quad (6)$$

where N is the total number of perturbed regions (equal to the number of Compton electrons) and A and d are the cross-section and the height of the detector, respectively. Along the horizontal (x) axis, within each "slice" the mesh elements are effectively connected in parallel, while the "slices" are in series. Within each slice, the effective capacitance is therefore $$\Delta C = \frac{\varepsilon_1 \varepsilon_0}{\Delta x}\left(A - \sum \Delta A\right) + \frac{\varepsilon_2 \varepsilon_0}{\Delta x}\left(\sum \Delta A\right), \quad (7)$$

where $\Delta x$ and $\Delta A = \Delta x^2$ are the element height and the cross-sectional area of each rectangular element, respectively; $\varepsilon_1$ and $\varepsilon_2$ are the effective dielectric constants of bulk PZT and the highly perturbed region, respectively. The sums are over the elements contained within each slice. With use of Eq. (6), Eq. (7) yields $$\Delta C = \frac{\varepsilon_0}{\Delta x}\left(A\varepsilon_1 - N\Delta A\left(\frac{\Delta x}{d}\right)(\varepsilon_1 - \varepsilon_2)\right). \quad (8)$$

The overall effective capacitance is obtained from all slices $$C_{\text{eff}} = 1 \bigg/ \left[\sum_{\left(\frac{d}{\Delta x}\right)} \frac{1}{\Delta C}\right], \quad (9)$$

resulting in a simple expression:

$$\varepsilon_{\text{eff}} = \varepsilon_1 - \frac{\Omega}{\Omega_t}(\varepsilon_1 - \varepsilon_2), \quad (10)$$

where Ω is the effective volume of all perturbed regions and $\Omega_t$ is the volume of the entire detector. The result is successfully reduced to phase-separate volumetric mixing. Here $\varepsilon_2 \ll \varepsilon_1$, as the transient volume distortion yields a large reduction in the dielectric constant and Eq. (10) reduces to $$\varepsilon_{\text{eff}} = \varepsilon_1\left(1 - \frac{\Omega}{\Omega_t}\right). \quad (11)$$

Using the above values, each single photon will result in $$\frac{\Omega}{\Omega_t} = 10^{-3},$$

or 0.1%. As the intrinsic dielectric constant of the material is high, the change is readily measurable through electronics based on resonance circuitry, or other forms.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus for detecting high energy electromagnetic radiation, the apparatus comprising:
  a detection pixel including a first material that is responsive to incident photons to produce:
    Compton electrons, and
    an electric or magnetic response in the first material caused by movement of the Compton electrons through the first material,
  wherein the incident photons and the Compton electrons each have a characteristic travel distance in the first material, and
  wherein the detection pixel has at least one dimension that is selected according to at least one of the characteristic travel distance of the incident photons and the characteristic travel distance of the Compton electrons.

2. The apparatus of claim 1 wherein the first material includes a ferroelectric material, a piezoelectric material, or a multiferroic material.

3. The apparatus of claim 1 wherein the first material includes at least one of titanates of lead, bismuth, barium, zirconium, and their alloys.

4. The apparatus of claim 1 wherein the first material includes at least one of a niobate and a tantalate.

5. The apparatus of claim 1 wherein the first material is responsive to photons in a first energy range to produce Compton electrons, wherein the first energy range is substantially between 20 KeV and 5 MeV.

6. The apparatus of claim 1 wherein the first material is selected to have an electric or magnetic response to incident photons in the x-ray frequency band.

7. The apparatus of claim 1 wherein the detection pixel is characterized by a cross-sectional dimension and a length, and wherein the cross-sectional dimension of the detection pixel is selected according to the characteristic travel distance of the Compton electrons.

8. The apparatus of claim 7 wherein the cross-sectional dimension of the detection pixel is at least one of a diameter, a side of a square, and a side of a rectangle.

9. The apparatus of claim 1 wherein the detection pixel is characterized by a cross-sectional dimension and a length, and wherein the cross-sectional dimension of the detection pixel is selected according to the characteristic travel distance of the incident photons.

10. The apparatus of claim 1 wherein the detection pixel is characterized by a cross-sectional dimension and a length, and wherein the length of the detection pixel is selected according to the characteristic travel distance of the incident photons.

11. The apparatus of claim 1 further comprising detection circuitry configured to measure the electric or magnetic response associated with the detection pixel.

12. The apparatus of claim 11 wherein the detection pixel and the detection circuitry form a resonant circuit having a resonance.

13. The apparatus of claim 12 further comprising circuitry configured to determine at least one property of the resonance.

14. The apparatus of claim 13 further comprising circuitry configured to determine at least one change in the at least one property of the resonance, wherein the determined at least one change corresponds to a passage of photons in the detection pixel.

15. The apparatus of claim 12 wherein the detection pixel is configured as an inductor or a capacitor in the resonant circuit, and wherein the detection circuitry is configured to measure a relative resonant frequency of the resonant circuit.

16. The apparatus of claim 15 wherein the detection circuitry is further configured to measure a change in the relative resonant frequency of the resonant circuit, wherein the change in the relative resonant frequency of the resonant circuit corresponds to a detection of photons by the detection pixel.

17. The apparatus of claim 1 wherein the detection pixel forms at least a portion of a capacitor having a capacitance, and wherein the capacitance is indicative of an interaction of photons with the detection pixel.

18. The apparatus of claim 1 wherein the detection pixel forms at least a portion of an inductor having an inductance, and wherein the inductance is indicative of an interaction of photons with the detection pixel.

19. A system for detecting high energy electromagnetic radiation the system comprising:

an array of detection pixels, each detection pixel in the array of detection pixels including a first material that is responsive to incident photons to produce:
Compton electrons, and
an electric or magnetic response in the first material caused by movement of the Compton electrons through the first material,
wherein the incident photons and the Compton electrons each have a characteristic travel distance in the first material, and
wherein each detection pixel in the array of detection pixels has at least one dimension that is selected according to at least one of the characteristic travel distance of the incident photons and the characteristic travel distance of the Compton electrons.

20. The system of claim 19 wherein each detection pixel in the array of detection pixels is separated from a subset of nearest neighbor detection pixels by a gap comprising a dielectric material.

21. The system of claim 19 wherein each detection pixel in the array of detection pixels includes a first material, and wherein the first materials of the detection pixels in the array are not all the same.

22. The system of claim 19 wherein the first material includes a ferroelectric material or a multiferroic material.

23. The system of claim 19 wherein the first material includes at least one of titanates of lead, bismuth, barium, zirconium, and their alloys.

24. The system of claim 19 wherein the first material includes at least one of a niobate and a tantalate.

25. The system of claim 19 wherein the first material is selected to have an electric or magnetic response to incident photons in the x-ray energy band.

26. The system of claim 19 wherein each detection pixel in the array is characterized by a cross-sectional dimension and a length, and wherein the cross-sectional dimensions of the detection pixels are selected according to at least one of the characteristic travel distance of the incident photons and the characteristic travel distance of the Compton electrons.

27. The system of claim 26 wherein the incident photons have a characteristic travel distance in the first material for a selected range of energies, and wherein the lengths of the detection pixels are selected according to the characteristic travel distance.

28. The system of claim 26 wherein the incident photons have a characteristic travel distance in the first material for a selected range of electromagnetic energies, and wherein the array has at least one dimension that is selected according to the characteristic travel distance.

29. The system of claim 26 wherein the cross-sectional dimension of the detection pixel is at least one of a diameter, a side of a square, and a side of a rectangle.

30. The system of claim 19 further comprising a source configured to produce the incident photons, wherein the array of detection pixels is arranged relative to the source to receive the photons produced by the source.

31. The system of claim 19 further comprising detection circuitry configured to measure the electric or magnetic response associated with at least two detection pixels in the array.

32. The system of claim 31 wherein the detection circuitry is configured to determine a relative amount of energy corresponding to the incident photons by comparing the electric or magnetic response of at least two detection pixels in the array.

33. The system of claim 31 wherein the detection circuitry is configured to produce an image corresponding to the incident photons by comparing the electric or magnetic response of at least two detection pixels in the array.

34. The system of claim 19 wherein the array of detection pixels is arranged to form an imaging device.

35. An x-ray imaging system for detecting high energy electromagnetic radiation, the x-ray imaging system comprising:
- a source of x-rays;
- an array of detection pixels, each detection pixel in the array of detection pixels including a first material that is responsive to the x-rays to produce:
  - Compton electrons, and
  - an electric or magnetic response in the first material caused by movement of the Compton electrons through the first material; and
- detection circuitry operably connected to the array of detection pixels that measures the electric or magnetic response in the first material produced by the Compton electrons.

36. The x-ray imaging system of claim 35 wherein the detection circuitry includes circuitry configured to compute a tomographic image of a subject.

37. The x-ray imaging system of claim 35 wherein at least one of the source of x-rays and the array of detection pixels is configured on a stage that is movable relative to a subject.

38. The x-ray imaging system of claim 37 wherein the at least one of the source of x-rays and the array of detection pixels is configured to scan the subject to create an image of the subject.

39. The x-ray imaging system of claim 35 wherein the detection circuitry is further configured to determine an energy corresponding to the x-rays received by the array of detection pixels.

40. The x-ray imaging system of claim 35 wherein the detection circuitry is further configured to determine an intensity corresponding to electromagnetic energy received by the array of detection pixels.

41. The x-ray imaging system of claim 35 wherein the detection circuitry is operably connected to the array of detection pixels and configured to measure a change in the dielectric constant of the first material.

42. The x-ray imaging system of claim 35 wherein the detection circuitry is operably connected to the array of detection pixels and configured to measure a change in the magnetic permeability of the first material.

* * * * *